United States Patent [19]

Kaschig et al.

[11] Patent Number: 5,294,735
[45] Date of Patent: Mar. 15, 1994

[54] SEMICARBAZIDES AND THE USE THEREOF FOR STABILIZING POLYAMIDE FIBRE MATERIALS AND THE DYEINGS PRODUCED THEREON

[75] Inventors: Jürgen Kaschig, Frieburg, Fed. Rep. of Germany; Gerhard Reinert, Allschwil, Switzerland; Georges Metzer, Moernach, France

[73] Assignee: Ciba-Geigy Corporation, Ardsley, N.Y.

[21] Appl. No.: 839,461

[22] Filed: Feb. 20, 1992

[30] Foreign Application Priority Data

Mar. 4, 1991 [CH] Switzerland ............... 637/91

[51] Int. Cl.$^5$ .............................. C07C 309/29
[52] U.S. Cl. ....................... 562/52; 562/46; 562/48; 544/159
[58] Field of Search ............ 564/34; 562/52, 48, 562/46

[56] References Cited

U.S. PATENT DOCUMENTS 3,630,987 12/1971 Thoma et al. ................ 564/34
3,755,443 8/1973 Sheppard et al. ............. 564/34

FOREIGN PATENT DOCUMENTS 3330190A 3/1985 Fed. Rep. of Germany ........ 564/34

OTHER PUBLICATIONS

Lipatov et al., CA 111:197297s (Abstract only, also attached is CAS Search copy), 1989.
Chem. Abstract, vol. 102, No. 20, CA 168277u, 1985.
Chem. Abstract, vol. 103, No. 12 CA 89053k, 1985.

Primary Examiner—Allen J. Robinson
Assistant Examiner—Shailendra Kumar
Attorney, Agent, or Firm—Marla J. Mathias; George R. Dohmann

[57] ABSTRACT

Novel semicarbazides of the formula

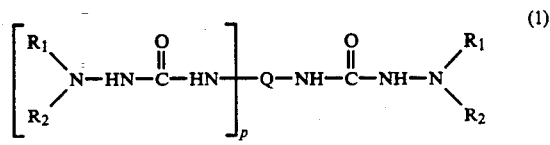

wherein $R_1$ and $R_2$, each independently of the other, are hydrogen, $C_1$-$C_5$alkyl, $C_2$-$C_5$alkenyl, $C_1$-$C_5$alkoxy or phenyl, or $R_1$ and $R_2$, together with the linking nitrogen atom, form a morpholine or piperazine radical, p is 0 or 1, and Q depends on the value of p as described herein. The novel compounds, which are water-soluble in aqueous application systems, have fibre affinity and are suitable for the photochemical and thermal stabilization of polyamide fibre materials and the dyeings produced thereon.

5 Claims, No Drawings

SEMICARBAZIDES AND THE USE THEREOF FOR STABILIZING POLYAMIDE FIBRE MATERIALS AND THE DYEINGS PRODUCED THEREON

The present invention relates to novel, water-soluble semicarbazides, to a process for the preparation of these compounds and to the use thereof for the photochemical and thermal stabilisation of polyamide fibres and the dyeing produced thereon.

Water-soluble semicarbazides which are able to stabilise fibres and and the dyeings obtained thereon are known. These compounds, however, have the drawback that they have no affinity for polyamide fibres and thus have insufficient fastness to water, washing, shampooing and dry cleaning. In addition, the potential applications of these compounds are limited to spraying or padding.

The semicarbazides of this invention, however, are water-soluble and simultaneously have fibre affinity and can be used in all conventional dyeing and aftertreatment processes to impart good wetfastness properties.

Specifically, the invention relates to semicarbazides of general formula

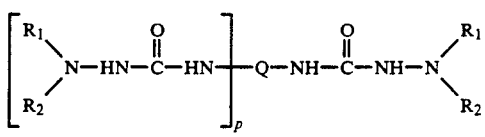

wherein
$R_1$ and $R_2$, each independently of the other, are hydrogen, $C_1$-$C_5$alkyl, $C_2$-$C_5$alkenyl, $C_1$-$C_5$alkoxy or phenyl, or $R_1$ and $R_2$, together with the linking nitrogen atom, are morpholino or piperazinyl,
p is 0 or 1,
when p=1, Q is a radical of formula

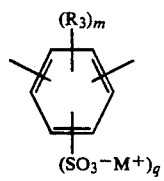

wherein
$R_3$ is hydrogen, $C_1$-$C_5$alkyl or halogen, m is 0,1,2 or 3,
q=1
or, when p=0,
Q is a radical of formula

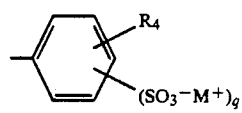

wherein
$R_4$ is hydrogen, $C_1$-$C_5$alkyl, halogen or a radical of formula

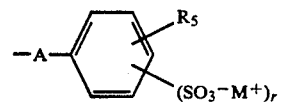

wherein $R_5$ is hydrogen, $C_1$-$C_5$alkyl or halogen,
M is hydrogen or alkali, and
A is —NH—, —O— or —SO$_2$—, and
q and r are 0 or 1, but are not simultaneously 0.

In the definition of the substituents $R_1$, $R_2$, $R_3$ and $R_5$ $C_1$-$C_5$alkyl and $C_1$-$C_5$alkoxy denote those groups or moieties which contain 1 to 5, preferably 1 to 3, carbon atoms. Exemplary of such groups are: methyl, ethyl, n-propyl, isopropyl, n-butyl, sec-butyl, tert-butyl, amyl or isoamyl and, respectively, methoxy, ethoxy, isopropoxy, isobutoxy, tert-butoxy or tert-amyloxy.

$C_2$-$C_5$Alkenyl is typically propenyl, butenyl or preferably allyl.

Halogen is fluoro, bromo or chloro. Chloro is preferred.

Typical examples of alkali metals are lithium, sodium or potassium. Sodium is preferred.

Phenyl may be substituted by one or more (SO$_3$-M$^+$) groups and $C_1$-$C_5$alkoxy by $C_1$-$C_5$alkoxy.

Morpholino and piperazinyl may be substituted by one or more $C_1$-$C_3$alkyl radicals.

Preferred compounds are those wherein $R_1$ and $R_2$ in formula 1 are $C_1$-$C_5$alkyl or, together with the linking nitrogen atom, form a morpholino ring,
Q is a radical of formula

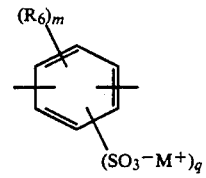

wherein
$R_6$ is $C_1$-$C_5$alkyl, and
M, m and q are as defined above.

If Q is a divalent radical, those compounds are especially preferred in which $R_1$ and $R_2$ are $C_1$-$C_5$alkyl and q is a radical of formula

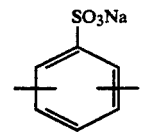

If Q is a monovalent radical, interesting compounds are those in which Q is a radical of formula

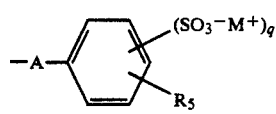

wherein
$R_5$ is $C_1$-$C_5$alkyl or halogen,
M is hydrogen or alkali, and
A is —SO$_2$— or —O—.

Particularly interesting semicarbazides are those wherein $R_1$ and $R_2$ in formula (1) are $C_1$-$C_5$alkyl and Q is a monovalent radical of formula

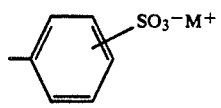 (3c)

wherein M is hydrogen or sodium.

The novel compounds are prepared by methods which are known per se, as for example those described in in Bull. Soc. Chim. France, p. D 12 et seq. (1954).

The novel semicarbazides are prepared by reacting 1 mol of 1,1'-carbonyldiimidazole with 1 mol of a hydrazine of formula

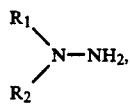

in anhydrous medium and in the presence of a polar, aprotic, water-miscible solvent in the temperature range from $-20°$ to $+20°$ C., preferably from $-10°$ to $0°$ C., and subsequently reacting the intermediate with 1 mol of the compound of formula Q—$NH_2$ or with 0.5 mol of the compound of formula $NH_2$—Q—$NH_2$, in a polar, water-miscible solvent or with a mixture of said solvents with water, in the temperature range from $-10°$ to $+80°$ C., preferably from $0°$ to $30°$ C., according to the reaction scheme

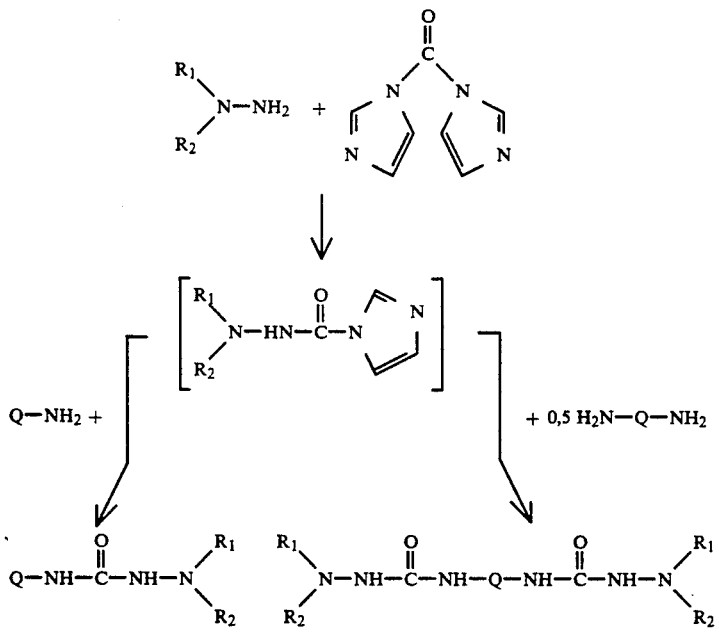

$R_1$ to $R_4$, M, Q, m and q in the above formulae have the same meanings as given for formulae (1), (2), (3) and (3a).

In the second step, suitable polar solvents which may be used as mixture together with water are water-soluble organic solvents.

Exemplary of such solvents are aliphatic $C_1$-$C_4$alcohols, such as methanol, ethanol or the propanols; alkylene glycols, such as ethylene glycol or propylene glycol; monoalkyl ethers of glycols, such as ethylene glycol monomethyl, monoethyl or monobutyl ether, and diethylene glycol monomethyl or monoethyl ether; ethers and acetals, such as diisopropyl ether, diphenyl oxide, dioxane, tetrahydrofuran, and also tetrahydrofurfuryl alcohol, pyridine, acetonitrile, γ-butyrolactone, N,N-dimethylformamide, N,N-dimethylacetamide, tetramethylurea and tetramethylenesulfone. Preferred solvents are tetrahydrofuran or N,N-dimethylformamide, and mixtures thereof with water.

An alternative mode of preparing the novel compounds of formula 1, wherein Q is defined such that $R_4$ is hydrogen, halogen or $C_1$-$C_5$alkyl, comprises reacting 1 mol of a hydrazine of formula

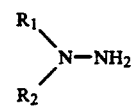

with 1 mol of an isocyanate of formula Q'—NCO, or with 0.5 mol of a diisocyanate of formula OCN—Q'—NCO, wherein $R_1$ and $R_2$ are as defined for formula (1) and Q' is the

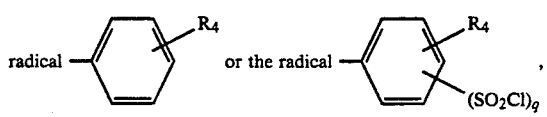

and Q" is the radical

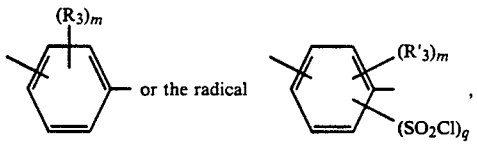

and, if Q' is the radical and Q" is the radical

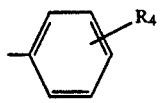

and Q" is the radical

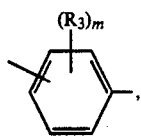

sulfonating the resultant intermediate, preferably with chlorsulfonic acid, to give the final product, and, if Q' is the radical

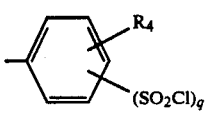

and Q" is the radical

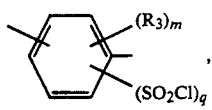

hydrolysing the intermediate to give the final product. In the above formulae, $R_3$, $R_4$, m and q are as previously defined. The reaction is carried out according to the following reaction scheme:

halogenated hydrocarbons, such as carbon tetrachloride. The preferred solvent is ethyl acetate.

The compounds of formula (1) are applied in the practice of this invention from an aqueous bath. They are water-soluble, when applicated in aqueous treating systems according to the present invention. The use of dispersants is not necessary. The amount of the compounds used will depend on the substrate and on the desired stabilisation. Normally 0.01 to 10%, preferably 0.1 to 5%, based on the substrate, will be used.

The application of the compounds can be made before, after or preferably during dyeing, by an exhaust process at liquor ratios of 1:5 to 1:500, preferably 1:10 to 1:50. The compounds are conveniently added to the dyebath.

The novel compounds can also be applied continuously by low application or high-temperature application systems.

In the continuous process, the liquor is conveniently applied to a pick-up of 30–400% by weight, preferably 75–250% by weight. To fix the dyes and the known and novel compounds the fibre material is subjected to a heat treatment. The fixation process can also be carried out by the cold pad-batch method.

The heat treatment is preferably carried out by steaming by treatment in a steamer with steam or superheated steam in the temperature range from 98°–105° C. for conveniently 1 to 7, preferably 1 to 5, minutes. The fixation of the dyes and the compounds of formula (1) by the cold pad-batch method can be effected by storing the impregnated and preferably rolled up goods at room temperature (15° to 30° C.), conveniently for 3 to 24 hours, the cold batching time depending naturally on the type of dye used.

When the dyeing process and fixation is complete, the dyeings are rinsed and dried in conventional manner.

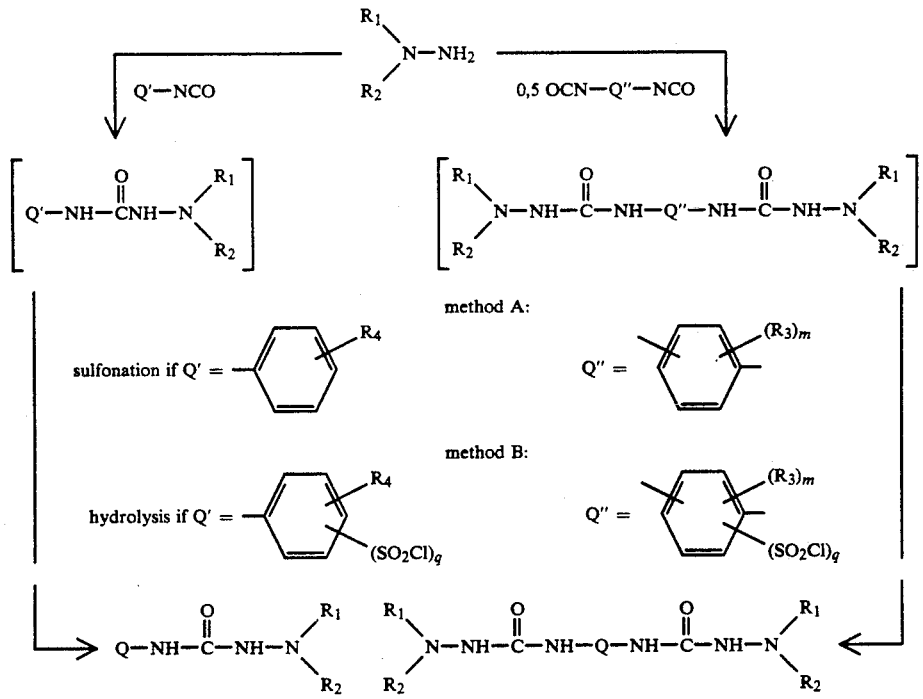

The intermediates are prepared by the standard methods, preferably by addition of hydrazines to isocyanates. Suitable solvents are carboxylates, such as acetates, and The novel semicarbazides are used for the photochemical and thermal stabilisation of polyamide fibre materials and the dyeings produced thereon. They are distinguished by good fibre affinity and impart good photochemical stability to the fibre materials treated with these compounds.

Polyamide fibre material will be understood as meaning in the context of this invention synthetic polyamide, typically polyamide 6, polyamide 66 or also polyamide 12. In addition to pure polyamide fibres, polyurethane/polyamide blends, for example tricot material made from polyamide/polyurethane in the ratio 70:30, are also suitable. Polypropylene/polyamide blends can also suitably be used. In principle, the pure polyamide material or blends thereof may be in various forms of presentation, including fibres, yarn, woven fabrics, knitted fabrics or carpets.

The novel compounds are particularly suitable for application to polyamide material and blends thereof with polyurethane or polypropylene which are exposed to the influence of light and heat, for example car upholstery, carpets or swimwear.

Dyeing is carried out in conventional manner conveniently with metal complex, anthraquinone or azo dyes and mixtures thereof. The metal complex dyes used are the known types, preferably the 1:2 chromium or 1:2 cobalt complexes of monoazo or disazo or azomethine dyes which are described in profusion in the literature. In addition to these dyes, dyes of other classes, such as disperse or also reactive dyes, may also suitably be used.

The invention is illustrated by the following Working and Use Examples in which parts and percentages are by weight. Unless otherwise indicated, the percentages of the ingredients of the individual dyebaths and treatment baths are based on the fibre material.

EXAMPLE 1

2,4-Bis(1,1-dimethylsemicarbazido-4)-benzenesulfonic acid, sodium salt

A solution of 3.6 g (0.06 mol) of 1,1-dimethylhydrazine in 20 ml of dimethylformamide is added dropwise at $-10°$ C. to a solution of 9.72 g (0.06 mol) of 1,1'-carbonyldiimidazole in 130 ml of dimethyl formamide. After stirring for 15 minutes at $-10°$ C., 4.2 g (0.02 mol) of 1,3-phenylenediamine-4-sulfonic acid, sodium salt, is added in increments. After stirring for 16 hours at room temperature, the bulk of the solvent is removed by distillation at 50° C. under a slight vacuum of about 0.13 Pa. The residue is boiled up with 300 ml of acetone and the precipitate is filtered with suction. The filter product is dried at 100° C. (c. 0.13 Pa), giving 5.63 g of the compound of formula

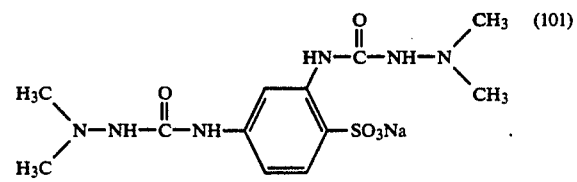

Yield: 76%; m.p. 230°-235° (decomp.)
Elemental analysis: found: 37.78% C; 4.87% H; 21.74% N; 8.04% S. calcd. for $C_{12}H_{19}N_6O_5SNa$: 37.69% C; 5.01% H; 21.98% N; 8.39% S.

EXAMPLE 2

2,6-Bis(1,1-dimethylsemicarbazido-4)-mesitylene-4-sulfonic acid, sodium salt

Following the general procedure of Example 1, 2.7 g (0.045 mol) o 1,1-dimethylhydrazine are reacted with 7.29 g (0.045 mol) of 1,1'-carbonyldiimidazole. Then 4.53 g (0.018 mol) of 2,6-diamino-mesitylene-4-sulfonic acid, sodium salt, dissolved in 25 ml of dimethyl formamide, are added dropwise. After stirring for 48 hours at room temperature, the reaction mixture is worked up. The residue obtained after distilling off dimethyl formamide is taken up at 55° C. with 75 ml of isopropanol. The product crystallises out from the cooled solution. Recrystallisation with water gives 6.5 g of the compound of formula

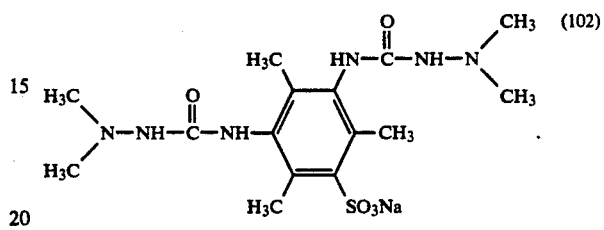

Yield: 85%; m.p. 250°-260°
found: 42.20% C; 6.1% H; 20.1% N; 7.4% S. calcd. for $C_{15}H_{25}N_6O_5SNa$: 42.45% C; 5.94% H; 19.80% N; 7.55% S.

EXAMPLE 3

4-(1,1-Dimethylsemicarbazido-4)-benzenesulfonic acid, sodium salt

In accordance with the procedure of Example 1, 1.28 g (0.0213 mol) of 1,1-dimethylhydrazine are reacted with 3.45 g of (0.0213 mol) of 1,1'-carbonyldiimidazole and 3.5 g (0.018 mol) of sulfanilic acid sodium salt. The reaction mixture is stirred for 24 hours at room temperature and the solvent is subsequently removed by distillation. The residue is stirred in 100 ml of isopropanol and the undissolved solid is isolated by filtration and recrystallised from 90 ml of water and dried at 60° C. (0.13 Pa), giving 4.0 g of the compound of formula

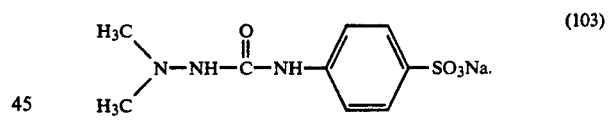

Yield: 79%; m.p. >300° C.
Elemental analysis: found: 38.2% C; 4.3% H; 15.0% N; 11.2% S. calcd. for $C_9H_{12}N_3O_4SNa$: 38.43% C; 4.30% H; 14.94% N; 11.39% S.

EXAMPLE 4

3-(1,1-Dimethylsemicarbazido-4)-benzenesulfonic acid sodium salt

A solution of 2.7 g (0.045 mol) of 1,1-dimethylhydrazine and 20 ml of tetrahydrofuran is added dropwise at 0° to 5° C. to a solution of 7.29 g (0.045 mol) of 1,1'-carbonyldiimidazole in 130 ml of tetrahydrofuran. After stirring for 15 minutes at 0° to 5° C., the reaction mixture is added to a solution of 6.23 g (0.036 mol) of metanilic acid, 36 ml of 1N sodium hydroxide solution and 10 g of ice. The precipitate formed is dissolved by addition of water. After stirring for 4 hours at room temperature the solution is concentrated to dryness and the residue is stirred in 200 ml of isopropanol. The residual powder is filtered with suction and dried, giving 7.35 g of the compound of formula

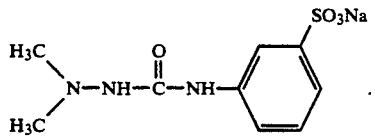

Yield: 72%; m.p. >300° C.

Elemental analysis: found: 38.5% C; 4.5% H; 14.6% N; 11.2% S. calcd. for C₉H₁₂N₃O₄SNa: 38.43% C; 4.30% H; 14.94% N; 11.39% S.

EXAMPLE 5

3-(1,1-Dimethylsemicarbazido-4)-benzenesulfonic acid 1.45 ml of 2N hydrochloric acid are added to 0.8 g (2.84 mol) of the compound of Example 4 in 2 ml of water. After stirring for 30 minutes at 0° C., the precipitate is filtered with suction and washed successively with 2N hydrochloric acid and ethanol and dried in an desiccator, giving 0.41 g of the compound of formula

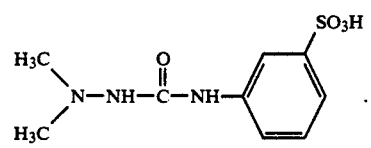

Yield: 56%; m.p. 205°–207° C.

Elemental analysis: found: 41.47% C; 4.97% H; 16.15% N; 12.42% S. calcd. for C₉H₁₃N₃O₄SNa: 41.69% C; 5.05% H; 16.21% N; 12.37% S.

EXAMPLE 6

2-(1,1-Dimethylsemicarbazido-4)-4,4'-dichlorodiphenyl ether-2'-sulfonic acid

In accordance with the procedure of Example 1, 2.7 g (0.045 mol) of 1,1-dimethylhydrazine are reacted with 7.29 g (0.045 mol) of 1,1'-carbonyldiimidazole. Then a suspension of 6.97 g (0.021 mol) of 2-amino-4,4'-dichlorodiphenyl ether-2'-sulfonic acid, sodium salt, in a minor amount of dimethyl formamide, is added. After stirring for 48 hours at room temperature and subsequently removing the solvent by distillation, 100 ml of water and 75 ml of 2N hydrochloric acid are added. The precipitate is filtered with suction, washed successively with 50 ml of 2N hydrochloric acid and with 400 ml of ice-water, and dried in an desiccator, giving 7.81 g of the compound of formula

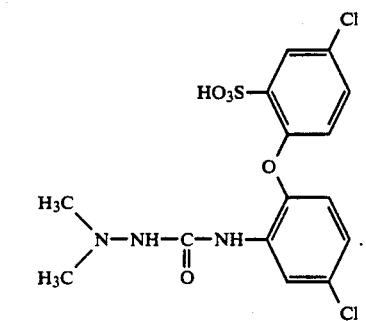

Yield: 89%; m.p. 272°–274° C.

Elemental analysis: found: 42.80% C; 3.80% H; 9.90% N; 7.40% S. calcd. for C₁₅H₁₅Cl₂N₃O₆S: 42.76% C; 3.82% H; 9.97% N; 7.61% S.

EXAMPLE 7

2-(1,1-Diaminosemicarbazido-4)-4'-methyldiphenylsulfone-4-sulfonic acid

In accordance with the procedure of Example 1, 2.7 g (0.045 mol) of 1,1-dimethylhydrazine are reacted with 7.29 g (0.045 mol) of 1,1'-carbonyldiimidazole. Then a solution of 3.95 g (0.0113 mol) of 2-amino-4'-methyldiphenylsulfone-4-sulfonic acid, sodium salt, in 50 ml of dimethyl formamide is added. Upon completion of the reaction, the reaction mixture is worked up as described in Example 6. For purification, the crude product is stirred for 2 hours in 150 ml of water, and the precipitate is filtered with suction and dried, giving 0.83 g of the compound of formula

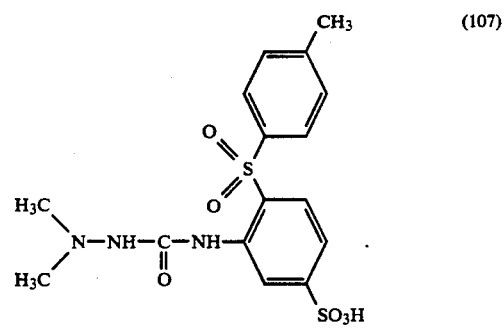

Yield: 18%; m.p. 260°–262° C. (decomp.)

Elemental analysis: found: 46.40% C; 4.60% H; 9.90% N. calcd. for C₁₆H₁₉N₃O₆S₂: 46.48% C; 4.63% H; 10.16% N.

EXAMPLE 8

2,4-Bis[1-(N-morpholino)-ureido-3]-benzenesulfonic acid sodium salt

In accordance with the procedure of Example 1, 4.59 g (0.045 mol) of N-aminomorpholine are reacted with 7.29 g (0.045 mol) of 1,1'-carbonyldiimidazole. Then a solution of 3.31 g (0.0157 mol) of 1,3-phenylenediamine-4-sulfonic acid sodium salt, in dimethyl formamide is added. The reaction mixture is stirred for 24 hours at room temperature and then worked up as described in Example 2. After drying there are obtained 5.77 g of the compound of formula

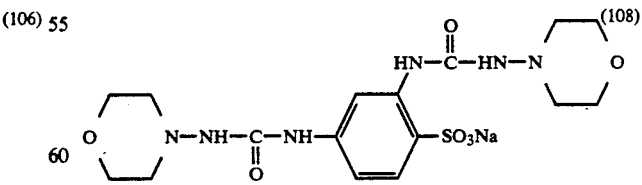

which contains crystalline isopropanol.

Yield: 76%; m.p. 256° C. (decomp.)

Elemental analysis: found: 42.0% C; 5.4% H; 17.1% N; 6.3% S; 4.56% Na. calcd. for C₁₆H₂₃N₆O₇SNa.1/3C₃H₈O: 42.0% C; 5.3% H; 17.3% N; 6.6% S; 4.76% Na.

EXAMPLE 9

4-(1,1-Dimethylsemicarbazido-4)-benzenesulfonic acid

A solution of 2.24 g (12.5 mmol) of 1,1-dimethyl-4-phenylsemicarbazide and 30 ml of ethyl acetate is added to a solution of 3 g (25.6 mmol) of chlorosulfonic acid and 30 ml of ethyl acetate. The reaction mixture is stirred for 10 minutes at 20° C. and for 15 minutes under reflux and the solvent is then distilled off under a slight vacuum at 40° C. The residue is stirred in 30 ml of ice-water. The precipitate is filtered with suction, washed with 10 ml of ice-water and dried in an desiccator, giving 2.59 g of the product of formula

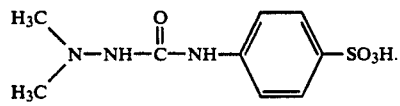 (109)

Yield: 80%; m.p. 230°-235° C. (decomp.)

Elemental analysis: found: 41.5% C; 5.1% H; 16.2% N; 12.2% S. calcd. for $C_9H_{13}N_3O_4S$: 41.69% C; 5.05% H; 16.21% N; 12.37% S.

APPLICATION EXAMPLES

EXAMPLE 10

Two 10 g samples of PA 6 knitgoods are dyed in an ®AHIBA dyeing machine at a liquor ratio of 1:25. Both dyebaths contain the following ingredients:
0.5 g/l of monosodium phosphate and
1.5 g/l of disodium phosphate, as well as the following dyes of formulae (I) and (II) dissolved in water:

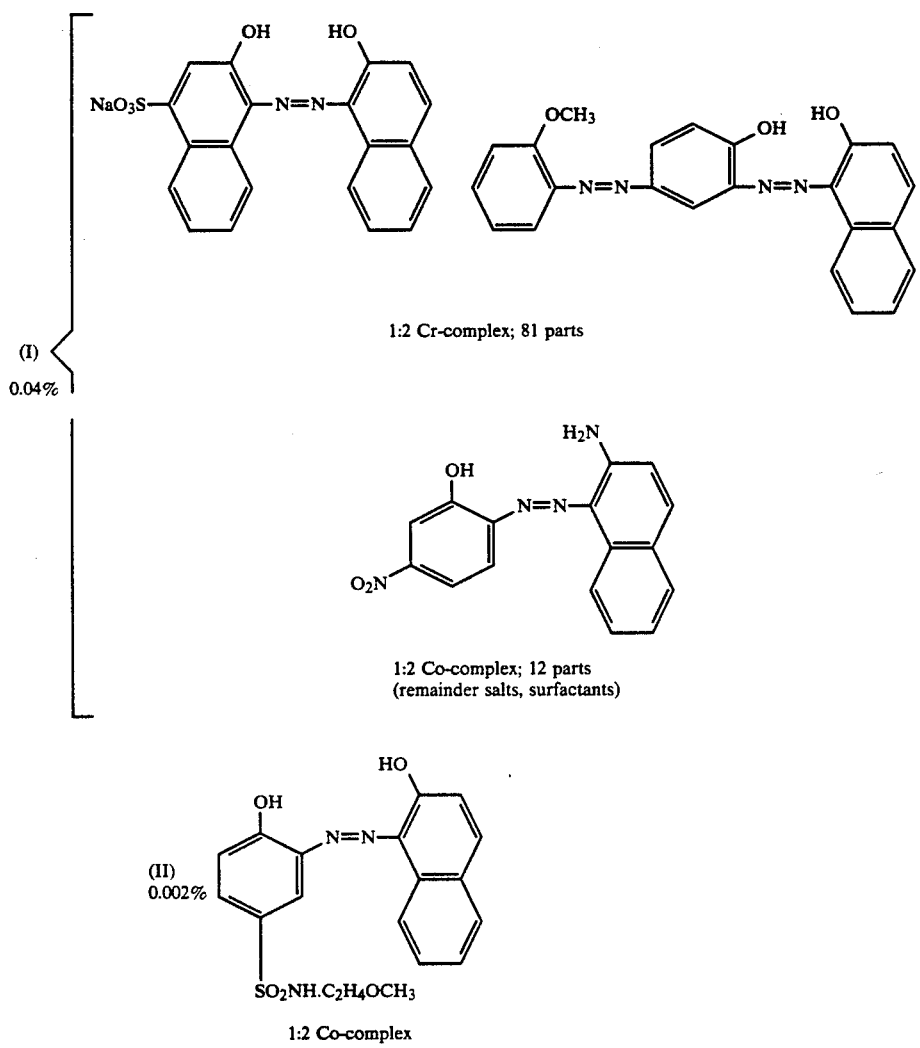

Whereas liquor 1 contains no further ingredients, liquor 2 additionally contains 1% of the compound of formula (101) dissolved in water.

The goods are put into these liquors at 40° C., batched for 10 minutes at this temperature and then heated at 2° C./min to 95° C. After a dyeing time of 20 minutes at 95° C., 2% of acetic acid (80%) are added and treatment is carried out for a further 25 minutes. After cooling to 60° C., the goods are rinsed with cold water, then centrifuged and dried at 120° C. for 2 minutes.

The dyeings are tested for their lightfastness properties according to SN-ISO 105-B02 (XENON) and DIN 75.202 (FAKRA). To determine the photochemical stabilisation, the dyeings are mounted on cardboard in samples measuring 12×4.5 cm and irradiated according to DIN 75.202. Their tear strength and stretch are determined according to SN 198.461.

EXAMPLES 11 TO 13

The procedure of Example 10 is repeated, using each of the following compounds:

EXAMPLE 11

1% of the compound of formula (103)

EXAMPLE 12

1% of the compound of formula (104)

EXAMPLE 13

1% of the compound of formula (107).

The dyeings are tested as described in Example 10. The results obtained in Examples 10–13 are reported in Table 1:

TABLE 1

| Addition to dyebath | Lightfastness 2 FAKRA cycles | Exposure 216 h FAKRA | |
|---|---|---|---|
| | | Tear strength [%] | Stretch [%] |
| none | 1H | 15.7 | 33.1 |
| + compound of formula (101) | 3–4 | 63.6 | 70.0 |
| + compound of formula (103) | 3–4 | 67.7 | 72.0 |
| + compound of formula (104) | 2–3 | 62.8 | 70.2 |
| + compound of formula (107) | 2 | 56.1 | 61.7 |

The use of the compounds of formulae (101), (103), (104) and (107) effects a marked enhancement of the photostability of substrate and dyeing as well as a substantial improvement in the lightfastness of the dyeings.

What is claimed is:

1. A semicarbazide of general formula $$\left[ \begin{matrix} R_1 \\ R_2 \end{matrix} N-HN-\overset{O}{\underset{\|}{C}}-HN \right]_p Q-NH-\overset{O}{\underset{\|}{C}}-NH-N\begin{matrix} R_1 \\ R_2 \end{matrix} \quad (1)$$

wherein
$R_1$ and $R_2$, each independently of the other, are $C_1$-$C_5$alkyl, $C_2$-$C_5$alkenyl, $C_1$-$C_5$alkoxy or phenyl,
p is 0 or 1,
when p=1, Q is a radical of formula (2) [phenyl ring with $(R_3)_m$ and $(SO_3^-M^+)_q$ substituents]

wherein
$R_3$ is hydrogen, $C_1$-$C_5$alkyl or halogen,
m is 0,1,2 or 3,
q=1
or, when p=0,
Q is a radical of formula (3) [phenyl ring with $R_4$ and $(SO_3^-M^+)_q$ substituents]

wherein $R_4$ is hydrogen, $C_1$-$C_5$alkyl, halogen or a radical of formula (3a) [−A−phenyl ring with $R_5$ and $(SO_3^-M^+)_r$ substituents]

wherein $R_5$ is hydrogen, $C_1$-$C_5$alkyl or halogen,
M is hydrogen or alkali, and
A is —NH—, —O— or —SO$_2$—, and q and r are 0 or 1, but are not simultaneously 0.

2. A semicarbazide according to claim 1, wherein $R_1$ and $R_2$ in formula 1 are $C_1$-$C_5$alkyl, Q is a divalent radical of formula (2a) [phenyl ring with $(R_6)_m$ and $(SO_3^-M^+)_q$ substituents]

wherein $R_6$ is $C_1$-$C_5$alkyl, and M, m and q are as defined in claim 1.

3. A semicarbazide according to claim 1, wherein $R_1$ and $R_2$ are $C_1$-$C_5$alkyl and Q is a divalent radical of formula (2b) [phenyl ring with SO$_3$Na substituent]

4. A semicarbazide according to claim 1, wherein Q is a monovalent radical of formula (3b) [−A−phenyl ring with $(SO_3^-M^+)_q$ and $R_5$ substituents]

wherein
$R_5$ is $C_1$-$C_5$alkyl or halogen,
M is hydrogen or alkali, and
A is —SO$_2$— or —O—.

5. A semicarbazide according to claim 1, wherein $R_1$ and $R_2$ in formula (1) are $C_1$-$C_5$alkyl and Q is a monovalent radical of formula (3c) [phenyl ring with SO$_3^-$M$^+$ substituent]

wherein M is hydrogen or sodium.

* * * * *